United States Patent [19]

Patel et al.

[11] Patent Number: 5,407,666

[45] Date of Patent: Apr. 18, 1995

[54] REMOVABLE, HARD, DURABLE, NAIL COATING

[75] Inventors: Naranbhai N. Patel, Orange; Debra Marr-Leisy, Long Beach, both of Calif.

[73] Assignee: International Beauty Design, Inc., Gardena, Calif.

[21] Appl. No.: 42,555

[22] Filed: Apr. 5, 1993

[51] Int. Cl.[6] .............................................. A61K 7/043
[52] U.S. Cl. .................................... 424/61; 424/78.03; 424/78.31; 427/508
[58] Field of Search .................... 424/61, 78.03, 78.31; 427/508; 524/560

[56] References Cited

U.S. PATENT DOCUMENTS

| | | | |
|---|---|---|---|
| 3,790,801 | 2/1974 | Coleman | 250/453.11 |
| 3,864,294 | 2/1975 | Busch, Jr. | 106/271 |
| 3,928,113 | 12/1975 | Roseberg | 156/344 |
| 4,057,657 | 11/1977 | Garnett et al. | 427/567 |
| 4,058,442 | 11/1977 | Lee, Jr. et al. | 522/33 |
| 4,135,526 | 1/1979 | Matranga et al. | 132/73 |
| 4,229,431 | 10/1980 | Lee, Jr. et al. | 424/61 |
| 4,495,175 | 1/1985 | Chavin et al. | 530/383 |
| 4,596,260 | 6/1986 | Giuliano | 132/73 |
| 4,626,428 | 12/1986 | Weisberg et al. | 424/61 |
| 4,682,612 | 7/1987 | Giuliano | 132/73 |
| 4,704,303 | 11/1987 | Cornell | 427/520 |
| 4,708,866 | 11/1987 | Turco et al. | 424/61 |
| 4,729,904 | 3/1988 | Berthet et al. | 424/487 |
| 4,762,703 | 8/1988 | Abrutyn | 424/61 |
| 4,871,534 | 10/1989 | Montgomery | 424/61 |
| 5,118,495 | 6/1992 | Nafziger et al. | 424/61 |
| 5,130,551 | 7/1992 | Nafziger et al. | 250/492.1 |

OTHER PUBLICATIONS

Barbara Ayash, The Professional Manicurist's Handbook, 1976.

Primary Examiner—D. Gabrielle Phelan
Assistant Examiner—Robert H. Harrison
Attorney, Agent, or Firm—William W. Haefliger

[57] ABSTRACT

A photocurable coating composition to be applied directly onto a nail surface and is rapidly curable upon exposure to ultraviolet light, comprising between 5% and 65% by weight of a film-forming polymer selected from the group consisting essentially of:
  i) cellulose derivatives
  ii) acrylic polymers;

between 2% and 20% by weight of a photoinitiator selected from the group consisting essentially of:
  i) acetophenone
  ii) benzophenone
  iii) alkylphenyl ketone
  iv) cyclohexylphenyl ketone;

and between 10% and 90% by weight of a photoreactive monomer selected from the group consisting essentially of:
  i) methacrylic acid esters
  ii) diesters of methacrylic acid, where the percentages by weight are based on the composition total weight.

1 Claim, 1 Drawing Sheet

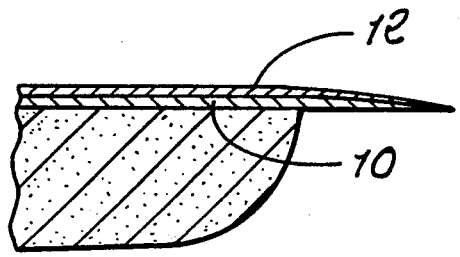
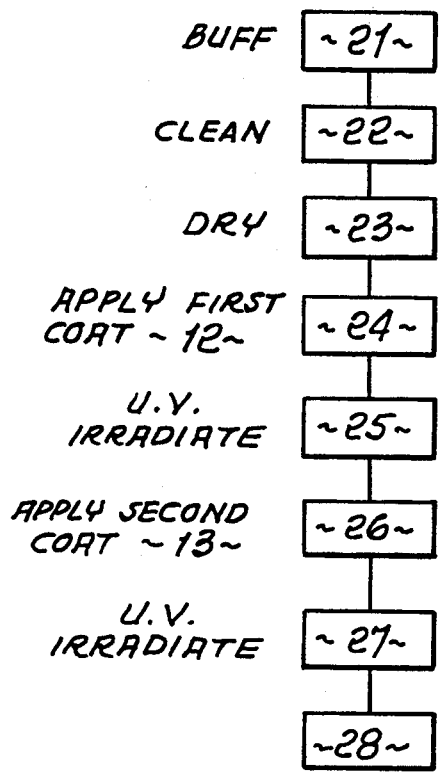
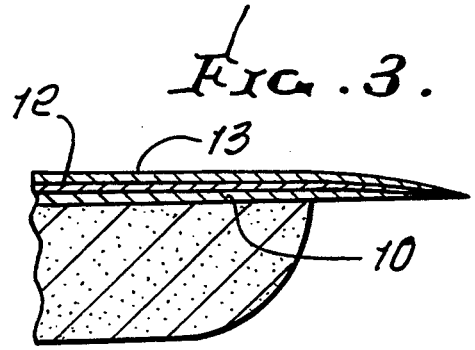
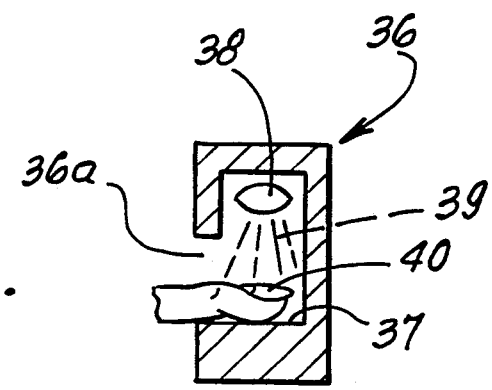

REMOVABLE, HARD, DURABLE, NAIL COATING

BACKGROUND OF THE INVENTION

This invention relates generally to nail coating compositions applicable to nails, such as fingernails and toenails; and more particularly, it concerns a photocurable, nail coating composition that is applied directly onto a nail surface, and then is hardened or is cured upon exposure to low-level, ultraviolet (UV) light.

There is need for a coating composition, as referred to, which, when applied directly onto a nail surface, is then curable faster than curing of standard polish, and which is also more durable than standard nail polish.

A further need is for such a protective coating which can be removed by application of conventional nail polish remover.

SUMMARY OF THE INVENTION

It is a major object of the invention to provide a composition which meets one or more, or all, of the above-referred needs.

Another object is to provide a photoreactive nail coating composition that requires only low levels of ultraviolet radiation to polymerize the photoreactive component in the coating.

A further object is to provide a photoreactive nail coating composition that dries to tack-free, smooth, shiny surface condition within only a few minutes of exposure to low-level, ultraviolet radiation.

Yet another object is to provide such a photoreactive nail coating composition that can be either pigmented or clear, and has enhanced wear characteristics as compared with conventional nail polish.

Additional objects include the provision of a photoreactive nail coating composition that can be directly applied to a natural nail or artificial nail (acrylic, nail tip, wrap, etc.); and that after curing by ultraviolet light, can be removed using standard, commercially available nail polish remover.

Basically, the composition of the invention, which meets the above needs, comprises:

a) between 5% and 65% by weight of a film-forming polymer selected from the group consisting essentially of:
 i) cellulose derivatives
 ii) acrylic polymers
b) between 2% and 20% by weight of a photoinitiator selected from the group consisting essentially of:
 i) acetophenone
 ii) benzophenone
 iii) alkylphenyl ketone
 iv) cyclohexylphenyl ketone
c) and between 10% and 90% by weight of a photoreactive monomer selected from the group consisting essentially of:
 i) methacrylic acid esters
 ii) diesters of methacrylic acid, where the percentages by weight are based on the composition total weight.

The composition may also contain minor amounts of a photoreactive substance, pigment or pigments, and solvent, as will be seen. Other ingredients may also be added to improve the handling or application of the coating. Examples are thickening agents, such as fumed silica, clay or pulverized glass, to modify viscosity; plasticizer, such as dibutyl phthalate, to increase flexibility of the cured coating; surfactants, slip agents, fragrance, etc.

The process of the invention includes applying the composition as a coating directly onto a nail surface, and then applying low-intensity, ultraviolet radiation to the coating, to cure same. The hardened coating may later be loosened, or removed, by application of commercially available nail polish remover. Such remover typically consists of solvent or solvents, such as acetone, ethyl alcohol, isopropyl alcohol, ethyl acetate, and methylethyl ketone.

These and other objects and advantages of the invention, as well as the details of an illustrative embodiment, will be more fully understood from the following specification and drawings, in which:

BRIEF DESCRIPTION OF THE DRAWINGS

FIG. 1 is a process flow diagram;

FIG. 2 is a vertical section taken through a fingernail onto which the photocurable coating has been applied;

FIG. 3 is like FIG. 2 but shows application of a second layer of the photocurable coating; and FIG. 4 is a vertical section showing ultraviolet radiation treatment of a coated fingernail, as in FIG. 2.

DETAILED DESCRIPTION

In FIG. 2, fingernail 10 is to undergo treatment. It is first prepared, as by standard practice used by nail technicians. For example, the nail is first buffed at 21 (in FIG. 1) to roughen its top surface. Next, it is cleaned at 22, as by application of a liquid solvent cleaner, preferably acetone, isopropyl alcohol, ethyl acetate, or butyl acetate, or some combination of these.

After drying, as indicated at 23, a first coating 12 of the composition of the invention is applied onto the dried surface of nail 10, this step shown at 24. The coated nail is then exposed to low-level, ultraviolet light, for about 30 seconds, this step seen at 25.

Next, the composition of the invention is applied as a second coating 13 (see step 26) onto the incompletely cured first layer 12, for binding therewith and curing of both upon exposure to ultraviolet light, as for 3 to 6 minutes. See step 27.

Alternatively, if one layer of coating is desired, that layer is applied directly to the nail surface and cured upon exposure to UV light for 3 to 6 minutes. Alternatively, if more than two layers of coating is desired, the initial layers are applied and incompletely cured upon exposure to UV light for 30 seconds. The final layer is applied to the incompletely cured coatings and cured upon exposure to UV light for 3 to 6 minutes. That composition, for each coat, comprises:

a) between 5% and 65% by weight of a film-forming polymer selected from the group consisting essentially of:
 i) cellulose derivatives
 ii) acrylic polymers
b) between 2% and 20% by weight of a photoinitiator selected from the group consisting essentially of:
 i) acetophenone
 ii) benzophenone
 iii) alkylphenyl ketone
 iv) cyclohexylphenyl ketone
c) and between 10% and 90% by weight of a photoreactive monomer selected from the group consisting essentially of:
 i) methacrylic acid esters ii) diesters of methacrylic acid, where the percentages by weight are based on the composition total weight.

The cellulose derivatives are selected from the group consisting essentially of cellulose esters, such as cellulose acetate, cellulose acetate propionate, and cellulose acetate butyrate, and nitrated derivatives of cellulose. The acrylic polymers are selected from the group consisting essentially of polymers and copolymers of methacrylic acid esters which include polymethylmethacrylate, polyethylmethacrylate, polybutylmethacrylate, polymethylmethacrylate-co-polyethylmethacrylate, and polymethylmethacrylate-co-polybutylmethacrylate; the methacrylic acid esters in the photoreactive monomer are selected from the group consisting essentially of ethyl methacrylate, cyclohexyl methacrylate, ethylhexyl methacrylate, butyl methacrylate, isobornyl methacrylate, and tetrahydrofurfuryl methacrylate; and the diesters of methacrylic acid are selected from the group consisting essentially of diethyleneglycol dimethacrylate, triethyleneglycol dimethacrylate, and 1,4-butanediol dimethacrylate.

The coating layers 12 and 13 may also, for best results, contain between 0% and 10% by weight photoreactive substance selected from the group consisting of epoxyacrylate oligomer, urethane acrylate oligomer, and vinyl ether; between 0% and 5% by weight pigment may be used; and between 0% to 40% weight solvent selected from the group consisting of isopropyl alcohol, isobutyl alcohol, ethyl acetate, butyl acetate, toluene, acetone, and methylethyl ketone. Sufficient such solvent is used to dissolve the nitrated cellulose, if that is employed. Between 0% and 10% by weight thickening agent selected from the group consisting of fumed silica, clay, and pulverized glass may be used.

FIG. 4 shows a fingernail 40, coated as described, inserted into a recess 36a in a receptacle 36, the finger 40a placed on a shelf 37 in the receptacle. An ultraviolet light bulb 38 at predetermined distance above the fingernail emits low-level, ultraviolet radiation 39 impinging on the nail. This treatment is carried out as referred to above. The resultant nail is presented at 28 in FIG. 1, in cleaned and hardened state.

A typical ultraviolet bulb 38 is of 4 watt power, delivers between 0.15 and 0.75 milliwatts per square centimeter (preferably about 0.5 milliwatts per cm$^2$) at the location of the fingernail, and at 350 nanometers wavelength. Two such bulbs are typically employed.

One preferred example of the composition seen at A in the following Table (which also includes formulas B to F) consists essentially of:

a) about 34% by weight polyethylmethacrylate-co-polymethylmethacrylate, b) about 9% by weight 2,2-dimethoxy-2-phenylacetophenone, c) about 54% by weight ethylmethacrylate, d) about 3% by weight pigment, where the percentages by weight are based on the composition total weight.

One usable pigment is quinacridone red. Others are Arylide red, Diarylide yellow, Titanium dioxide white, D & C red #7, D & C red #6, #6 Barium Lake, Iron oxide or oxides, and D & C violet #2.

| INGREDIENT | FORMULATION (Wt %) | | | | | |
|---|---|---|---|---|---|---|
| | A | B | C | D | E | F |
| Cellulose Acetate Butyrate | | 20 | 30 | | 40 | 15 |
| Polymethylmethacrylate-co-Polyethylmethacrylate | 34 | | 15 | | | |
| 2,2-Dimethoxy-2-Phenylacetophenone | 9 | 10 | 5 | 10 | 15 | 5 |
| Ethyl Methacrylate | 54 | 70 | 32 | 71 | 45 | 15 |
| Diethyleneglycol Dimethacrylate | | | 3 | | | 5 |
| Fumed Silica | | | | 3 | | |
| Ethyl Acetate | | | 15 | | | 45 |
| Isopropyl Alcohol | | | | | | 5 |
| Butyl Acetate | | | 15 | | | 10 |
| Pigment | 3 | | 1 | | | |

In the above, 2,2-dimethoxy-2-phenylacetophenone is a commercially available photoinitiator and is in the family of alkylphenyl ketone photoinitiators.

After formation of the protective, hardened coating 13, as referred to, it and cured layer 12 may easily be loosened and removed by application of standard, conventional nail polish remover, examples consisting of acetone, ethyl alcohol, isopropyl alcohol, ethyl acetate, butyl acetate, and methylethyl ketone.

It was found to be surprising that film-forming polymers with such diverse chemistries as cellulose derivatives and acrylic polymers are compatible with other components of the composition or compositions defined above. This compatibility allows increased latitude in tailoring the physical properties of the cured coating.

We claim:

1. A photocurable coating composition applied directly onto a nail surface and which is rapidly curable upon exposure to ultraviolet light, consisting of:
   a) between 5% and 65% by weight of a film-forming polymer selected from the group consisting of:
   polymethylmethacrylate
   polyethylmethacrylate
   polybutylmethacrylate
   polymethylmethacrylate-co-polyethylmethacrylate
   and polymethylmethacrylate-co-polybutylmethacrylate
   b) between 2% and 20% by weight of a photoinitiator selected from the group consisting of:
   i) acetophenone
   ii) benzophenone
   iii) alkylphenyl ketone
   iv) and cyclohexylphenyl ketone
   c) between 10% and 90% by weight of a photoreactive monomer selected from the group consisting of:
   ethyl methacrylate
   cyclohexyl methacrylate
   ethylhexyl methacrylate
   butyl methacrylate
   isobornyl methacrylate
   tetrahydrofurfuryl methacrylate
   diethyleneglycol dimethacrylate
   triethyleneglycol dimethacrylate
   and 1,4-butanediol dimethacrylate
   d) between 0% to 10% by weight photoreactive substance selected from the group consisting of:
   epoxyacrylate oligomer
   urethane acrylate oligomer
   and vinyl ether
   e) between 0% to 10% by weight thickening agent selected from the group consisting of:
   fumed silica
   clay
   and pulverized glass,
   f) and between 0% to 5% by weight pigment.

* * * * *